(12) United States Patent
Young

(10) Patent No.: US 8,457,983 B2
(45) Date of Patent: Jun. 4, 2013

(54) REVENUE SHARING BY A PRINTER MANUFACTURER FOR SALES OF PRESCRIPTION DRUGS

(75) Inventor: Chihsin Steven Young, Irvine, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 619 days.

(21) Appl. No.: 12/405,506

(22) Filed: Mar. 17, 2009

(65) Prior Publication Data

US 2010/0241444 A1    Sep. 23, 2010

(51) Int. Cl.
  *G06Q 10/00*  (2012.01)
  *G06F 19/00*  (2011.01)
(52) U.S. Cl.
  USPC .................................................. 705/2; 705/3
(58) Field of Classification Search
  USPC .............................. 705/2, 3–4, 14
  See application file for complete search history.

(56) References Cited

U.S. PATENT DOCUMENTS

| | | | |
|---|---|---|---|
| 6,321,208 B1 | 11/2001 | Barnett et al. | |
| 6,882,442 B2* | 4/2005 | Roberts ........................... | 358/1.2 |
| 6,954,732 B1 | 10/2005 | DeLapa et al. | |
| 6,970,835 B1 | 11/2005 | Forward | |
| 6,985,452 B2 | 1/2006 | Marshall et al. | |
| 7,188,154 B2 | 3/2007 | Minowa | |
| 7,899,686 B1* | 3/2011 | Akers et al. ....................... | 705/3 |
| 2002/0055856 A1 | 5/2002 | Adams | |
| 2002/0077893 A1 | 6/2002 | Wolf et al. | |
| 2003/0036683 A1* | 2/2003 | Kehr et al. ..................... | 600/300 |
| 2003/0050799 A1* | 3/2003 | Jay et al. ........................... | 705/2 |
| 2004/0002872 A1 | 1/2004 | Wright | |
| 2004/0172295 A1 | 9/2004 | Dahlin et al. | |
| 2004/0236630 A1 | 11/2004 | Kost et al. | |
| 2007/0255618 A1* | 11/2007 | Meerbergen et al. ........... | 705/14 |

* cited by examiner

*Primary Examiner* — Hiep V Nguyen
(74) *Attorney, Agent, or Firm* — Fitzpatrick, Cella, Harper & Scinto

(57) ABSTRACT

Sharing in the revenues for the sale of prescription drugs in a system comprising an interactive advertising/printing device of a printer manufacturer, a pharmacy and a prescription drug manufacturer. An advertisement of a prescription drug is displayed on the interactive advertising/printing device, and a patient utilizing the interactive advertising/printing device print out a partial prescription for a prescription drug based on the advertisement. The printed partial prescription for the prescription drug is provided to an individual authorized to issue prescriptions for medical drugs, whereby the individual authorized to issue prescriptions completes the partial prescription, which is then provided to the pharmacy for fulfillment. The pharmacy inputs information of the completed prescription into a database, fulfils the prescription for the patient, and completes a sales transaction with the patient for the fulfilled prescription. The sales transaction information for the fulfilled prescription is transmitted to the prescription drug manufacturer, whereby the prescription drug manufacturer determines, based on the sales transaction information, an amount of revenue to share with the printer manufacturer. The prescription drug manufacturer provides the determined amount of the revenue for the sale of the prescription drug to the printer manufacturer.

13 Claims, 5 Drawing Sheets

REVENUE SHARING BY A PRINTER MANUFACTURER FOR SALES OF PRESCRIPTION DRUGS

BACKGROUND OF THE INVENTION

1. Field of the Invention

The invention generally concerns the sharing of revenue for the sales of prescription drugs, and more specifically, the invention relates to an interactive advertising/printing system in which profits for prescription drug sales can be shared between a drug manufacturer and a printer manufacturer. In more detail, the invention provides a system for a printer manufacturer to share in the profits for the sales of prescription drugs if a patient prints out a partial prescription via an interactive advertising/printing system that advertises the drug, has the prescription completed and validated by a doctor, and then has the prescription fulfilled by a pharmacy.

2. Description of the Related Art

Conventionally, it has been known to provide a medical patient with a discount for medical supplies based on the patient's medical profile. One example of a conventional system has been described in U.S. Patent Publication No. 2003/0050799 to Jay et al. (hereinafter referred to simply as "Jay"), entitled "Permission Based Marketing For Use With Medical Prescriptions".

The system in Jay includes a "doctors side", and an "industry side". The industry side may include an employer database, a healthplan database, a PBM database, a pharmacy database, and an RxChange server, while the doctors side may include a PPM (Physician Practice Management Data Database), and other local network components such as printer, local server, PDA, etc. The industry side and the doctors side communicate via various internet components. The system of Jay maintains the patient's medical history and allows the doctor to print out prescriptions for the patient. Once the prescription is printed out by the doctor, the system can provide a list of pharmacies for the patient to visit in order to fulfill the prescription. The system of Jay also includes the ability to print out coupons or advertisements related to the medication prescribed by the doctor. Thus, while not explicitly disclosed in Jay, it is possible that the doctor, the pharmacy and the coupon vendor may be able to share in the profit for the sale of the medication, but there is no provision for the printer manufacturer to share in the profits.

SUMMARY OF THE INVENTION

The invention addresses the foregoing by providing a system for a printer manufacturer to share in the profits for the sales of prescription drugs if a patient prints out a partial prescription via an interactive advertising/printing system that advertises the drug, has the prescription completed and validated by a doctor, and then utilizes the printed prescription to have a pharmacy fulfill the drug order. In one example embodiment, a doctor's office may have an interactive advertising/printing system in which advertisements for drugs are displayed. A patient waiting to see the doctor may view the advertisement and may want to obtain a prescription for the advertised drug. To obtain the prescription, the patient utilizes the interactive advertising/printing system to print out a partial prescription for the drug. The partial prescription may include information about the name of the drug, but portions such as the patient's name, dosage and doctor's signature may be left blank. The partial prescription is then provided to the doctor, whereby the doctor completes the prescription. The completed prescription is then provided to a pharmacy to have the order filled, or the doctor can transmit the completed prescription directly to the pharmacy.

To share in profits for the sale of the drug, the prescription may include, for example, a bar code. The bar code may link to a database that identifies the manufacturer of the advertising/printing system from which the patient printed out the prescription. When the prescription is provided to the pharmacy, the bar code may be scanned-in and the information included therein regarding the manufacturer of the advertising/printing system, as well the sales amount for the prescription, provided to the drug manufacturer. Alternatively, the information can be obtained from an electronic file for the prescription that is provided electronically by the doctor directly to the pharmacy. The drug manufacturer can thereafter return a portion of the profit for the sale of the drug utilizing the interactive advertising/printing system to the printer manufacturer. The drug manufacturer can also utilize the information to track the number of sales of a particular drug via the advertising/printing system so as to be able to track the effectiveness of the advertising.

Thus, in aspect, the invention is directed to a method of sharing in the revenues for the sale of prescription drugs in a system comprising an interactive advertising/printing device of a printer manufacturer, a pharmacy and a prescription drug manufacturer. In the method of the invention, an advertisement of a prescription drug is displayed on the interactive advertising/printing device, and a patient utilizing the interactive advertising/printing device prints out a partial prescription for a prescription drug based on the advertisement. The printed partial prescription for the prescription drug is provided to an individual authorized to issue prescriptions for medical drugs, whereby the individual authorized to issue prescriptions completes the partial prescription, which is then provided to the pharmacy for fulfillment. The pharmacy inputs information of the completed prescription into a database, fulfils the prescription for the patient, and completes a sales transaction with the patient for the fulfilled prescription. The sales transaction information for the fulfilled prescription is transmitted to the prescription drug manufacturer, whereby the prescription drug manufacturer determines, based on the sales transaction information, an amount of revenue to share with the printer manufacturer. The prescription drug manufacturer provides the determined amount of the revenue for the sale of the prescription drug to the printer manufacturer.

In one representative embodiment, the interactive advertising/printing device comprises an interactive touch-screen television connected to a printer, wherein the patient prints-out the partial prescription utilizing the touch-screen television. In addition, the partial prescription includes the name of the drug and includes blank spaces for the patient's name, dosage and a signature of the individual authorized to issue prescriptions, and is printed with a bar code associated with the printer manufacturer of the interactive advertising/printing system. The pharmacy scans-in the bar code and transmits printer manufacturer information associated therewith, along with a sales amount for the prescription to the prescription drug manufacturer. The drug manufacturer may also maintain a record of the number and type of prescriptions fulfilled by the pharmacy in correspondence with identification information of the interactive advertising/printing device. In this manner, the drug manufacturer can track whether or not a particular interactive system is effective, and which drugs are being prescribed more often than others at each location where the interactive systems are installed.

This brief summary has been provided so that the nature of the invention may be understood quickly. A more complete understanding of the invention can be obtained by reference to the following detailed description of the preferred embodiments thereof in connection with the attached drawings.

DETAILED DESCRIPTION OF THE PREFERRED EMBODIMENTS

Figure 1:
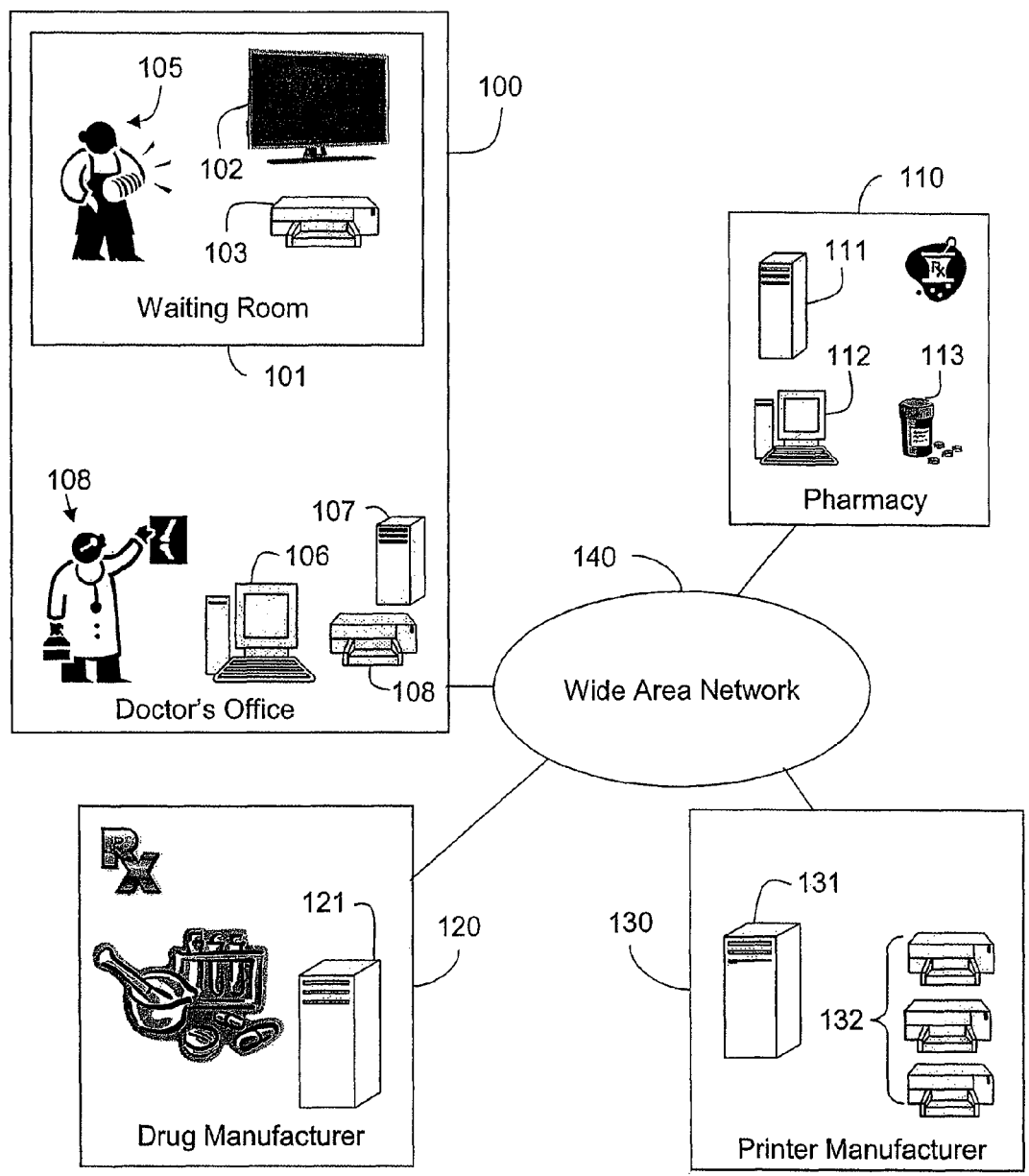
FIG. 1 depicts an example environment in which the invention may be implemented.

FIG. 1 depicts an example environment in which the invention may be implemented. Briefly, the drug advertisements are displayed on an interactive system, where by a patient can use the interactive system to print out a partial prescription that can be presented to the doctor. After the doctor completes the prescription, a pharmacist fulfills the prescription and inputs the prescription and sales information. The prescription and sales information is then provided to the drug manufacturer, who can determine how much of the sales revenue to return to the interactive system/printer manufacturer.

Referring to FIG. 1, the invention can be seen to be implemented in an environment that includes a doctors office 100, a pharmacy 110, a drug manufacturer 120 and a printer manufacturer 130, each of which may communicate via network 140. Network 140 is preferably a wide area network (WAN) such as the Internet, but it may also be local area network (LAN) instead. Doctors Office 100 includes a waiting room 101 where, as is common, patients wait for their turn to see a doctor. While the patients are waiting in the waiting room, an interactive advertisement/printing system may be functional to display advertisements or infomercials about various drugs or medications. Such an interactive advertisement/printing system may include a display 102, such as a flat panel television, and a printer 103, both of which may be connected to each other and to a server 107 in the doctors office. The display 102 may include a touch screen functionality that provides the ability for a patient to interact with the system to select various functions displayed on the display. The display 102 may include remote control functionality that provides the ability for a patient to interact with the system to select various functions displayed on the display. As will be described in more detail below, one function that may be displayed on the display is for the patient to print out a partial prescription of a drug or medication. While depicted in FIG. 1 as a display monitor, it can readily be understood that display 102 may be an all-in-one type of device that has a built-in processor and memory that stores and executes programs of various types, including an interactive program utilized in the invention. That is, display 102 may be a monitor that merely displays an interactive program that is run by software code stored in and executed by, for example, server 107, but the server functionality may also be incorporated in the hardware of display 102 itself.

As part of the interactive system seen in FIG. 1, printer 103 is included in the waiting room. As will be described in more detail below, when a patient interacts with the interactive system and selects a function to print out a partial prescription of a drug or medication, the partial prescription is printed on printer 103. The patient can then present the printed out partial prescription to the doctor. However, as an alternative, the partial prescription may be printed electronically to a file, with the file being forwarded to a doctor or administrator.

The doctor's office 100 is also seen to include server 107, computer workstation 106 and printer 108, each of which may be connected to one another. In addition, computer workstation 106 and server 107 may be connected to network 140. Server 107 will be described in more detail below, but as can readily be understood, various programs for running a medical office may be executed by server 107, and various records, such as patient files, prescriptions issued by the doctor, etc., may be maintained on server 107. One program that may be included in server 107 provides the ability for the doctor's office to electronically provide a completed prescription directly to a pharmacist for the pharmacist to fulfill the prescription. Computer workstation 106 may likewise be utilized to store and execute various programs for running the doctor's office, and may also communicate directly with other computers on the network.

Pharmacy 110 is also depicted in FIG. 1. While only one pharmacy is shown in the environment of FIG. 1, it can readily be understood that more than one pharmacy may be included in the network, and the single pharmacy 110 shown in FIG. 1 is merely for representative purposes. Pharmacy 110 is seen to include computer workstation 112 and server 111. Either or both of computer workstation 112 and server 111 may execute any of various computer programs for operating a pharmacy, including maintaining drug or medication inventory data, patient information such as the patient's name, type of medication prescribed, amount of the drug or medication prescribed, the cost of fulfilling the prescription, etc. Without violating patient privacy or confidentiality, server 111 or workstation 112 of pharmacy 110 may also provide information regarding the type of drug prescribed, identification of the doctor that prescribed the drug, the amount of drug prescribed, and the sales cost of fulfilling the prescription to drug manufacturer 120. As will be described below, this information may be utilized by drug manufacturer 120 to determine how much of the sales price, or profit for the sale of the drug, to share with others, including the manufacturer of the printer or interactive system from which the prescription originated.

The environment of FIG. 1 is also seen to include drug manufacturer 120 and printer manufacturer 130. Drug manufacturer 120 is preferably a company that manufactures and sells drugs or medications under approval of the United States Food and Drug Administration (FDA). The drugs or medications may be brand name drugs or medicines approved by the FDA via a New Drug Application (NDA), or may be a generic-type drug or medicine approved by the FDA via an Abbreviated New Drug Application (ANDA). Regardless of whether the drug or medication is a brand name or a generic-type, in practicing the invention, the drug or medication is one that preferably requires a prescription from a licensed medical professional, such as a medical doctor, or any other type of professional that is licensed or authorized to issue prescriptions for drugs or medications. When drugs or medications manufactured by drug manufacturer 120 are prescribed by a doctor and sold by a pharmacy to a patient, the drug manufacturer may be notified of the sale by the pharmacy. In this manner, the drug manufacturer may be able to track drug sales in particular locales so they know which of their drugs are sold most often in that locale. With this sales data, the drug manufacturer can formulate a better marketing plan for their drugs to each locale, including a determination of which interactive advertisements are the most effective in each locale. In addition, the drug manufacturer can track the sales volume of each drug in correlation with the interactive system from which the prescription was initiated. That is, when the partial prescription is printed by the patient using the interactive system, data may be printed on the partial prescription identifying the interactive system. Then, when the prescription is fulfilled by the pharmacist, the drug manufacturer can determine the interactive system/printer manufacturer associated with the prescription so they will be able to determine the printer manufacturer that a portion of the revenue for the drug sale will be credited to.

Thus, as also seen in FIG. 1, the system of the invention includes printer manufacturer 130. Printer manufacturer 130 is preferably a company that manufactures printers to be utilized in the interactive system of the invention, such as Canon®. That is, in order for the drug manufacturer to help promote the sales of its drugs, it enters into a revenue sharing agreement with the printer manufacturer. The printer manufacturer, as part of the revenue sharing agreement, provides the printer for each interactive system, and may also provide the interactive system itself. Thus, the drug manufacturers can engage the printer manufacturers to install and maintain the interactive systems, and in exchange, will share a portion of the sales revenue for drugs prescribed and sold via the interactive system with the printer manufacturer.

Figure 2:
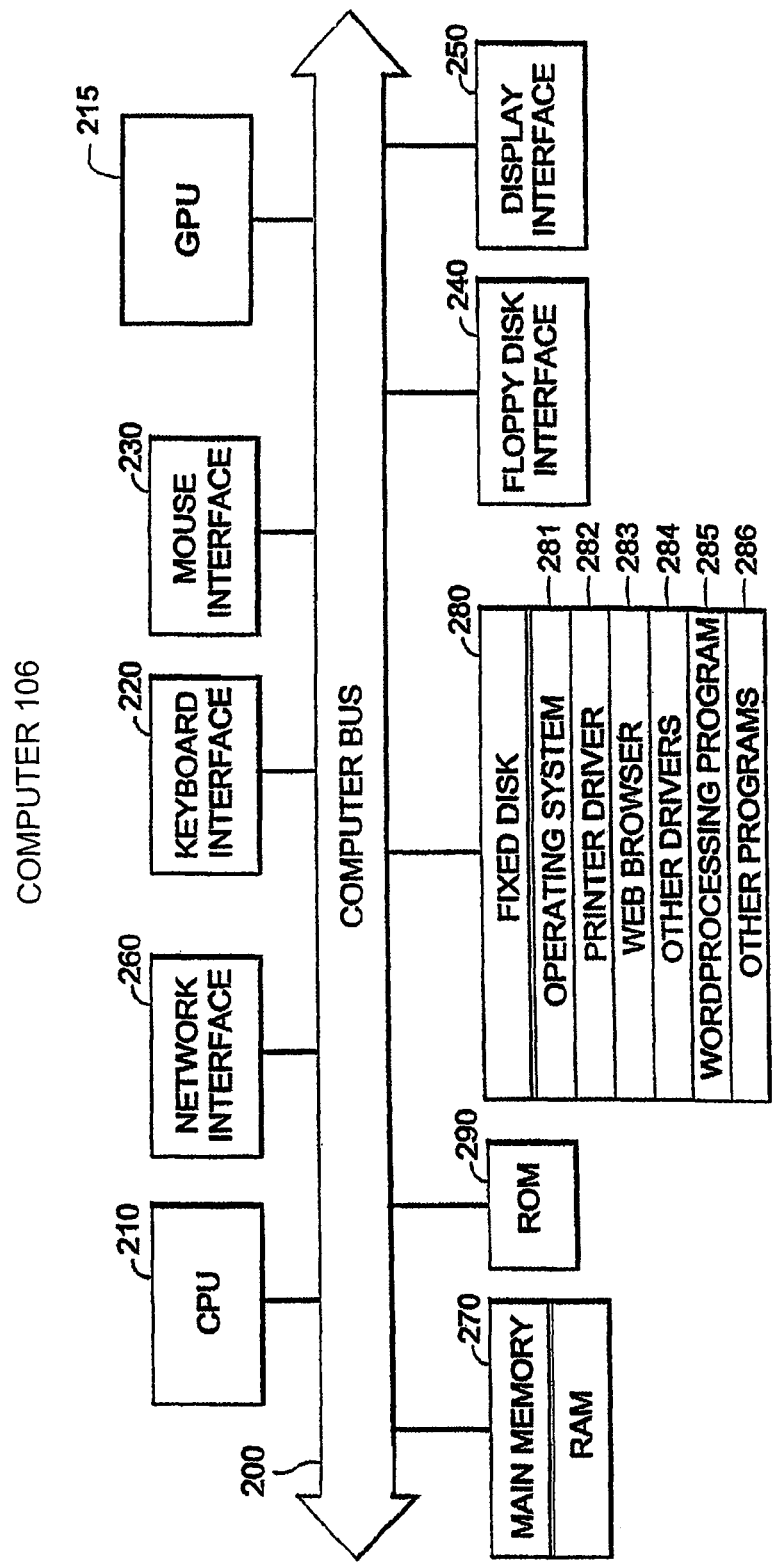
FIG. 2 depicts an internal architecture of a computer workstation.

Referring now to FIG. 2, depicted therein is a block diagram showing an example of the internal architecture of a computer workstation, such as workstation 106. The architecture shown in FIG. 2 may be equally applicable to other workstations in the system of the invention, including computer workstation 112 of pharmacy 110, or an all-in-one display 102. In FIG. 2, workstation 106 is seen to include central processing unit (CPU) 210 such as a programmable microprocessor which is interfaced to computer bus 200. A graphics processing unit (GPU) 215 is also coupled to computer bus 2300, where the GPU controls a graphical display program for displaying graphics on a display device. In particular, GPU 215 may implement the interactive program processing of the invention so as to control displaying an interactive drug advertisement on a display device 102. Also coupled to computer bus 200 are keyboard interface 220 for interfacing to a keyboard, mouse interface 230 for interfacing to a mouse or other pointing device, floppy disk interface 240 for interfacing to a floppy disk, CD-ROM drive (not shown), flash drive, etc., display interface 250 for interfacing to a monitor or other display device, and network interface 260 for interfacing to a network, such as Wide Area Network (Internet) 140. Interface 260 may be, for example, a 56K modem, a DSL modem, a cable modem, an Ethernet card that may or may not communicate with an external modem, a wireless interface (e.g., Bluetooth interface, infrared interface), etc.

Random access memory (RAM) 270 interfaces to computer bus 200 to provide CPU 210 with access to memory storage, thereby acting as the main run-time memory for CPU 210. In particular, when executing stored program instruction sequences, such as an interactive drug advertisement program of the invention that may be stored in fixed disk 280, a CD-ROM interfacing with workstation 106, etc., CPU 210 loads those instruction sequences from fixed disk 280 (or other memory media) into RAM 270 and executes those stored program instruction sequences out of RAM 270. It should also be noted that standard disk swapping techniques available under windowing operating systems allow segments of memory to be swapped to and from RAM 270 and fixed disk 280. Read-only memory (ROM) 290 stores invariant instruction sequences, such as start-up instruction sequences for CPU 210 or basic input/output operation system (BIOS) sequences for the operation of peripheral devices (not shown) attached to workstation 106.

Fixed disk 280 is one example of a computer-readable storage (memory) medium that stores program instruction sequences executable by CPU 210. The program instructions may constitute windows operating system 281, printer driver 282, web browser 283, other drivers 284, word processing program 285, and other programs 286. Among other programs 286, the interactive drug advertisement/partial prescription printing program of the invention may be stored therein to be executed by workstation 106 in conjunction with display 102. Operating system 281 is preferably a windows operating system, although other types of operating systems may be used with the present invention. Printer driver 282 is utilized to prepare image data for printing on at least one image forming device, such as printer 103 or 108. Web browser application 283 is preferably a browser application such as Windows Internet Explorer®, Mozilla Firefox®, or Safari™, although other web browser applications may be utilized instead. Other drivers 284 include drivers for each of the remaining interfaces which are coupled to computer bus 200. Word processing program 285 is a typical word processor program for creating documents and images, such as Microsoft®Word, or Corel®WordPerfect documents. Other programs 286 contains other programs necessary to operate workstation 106 and to run desired applications, such as the interactive drug advertisement/partial prescription printing program of the invention.

Figure 3:
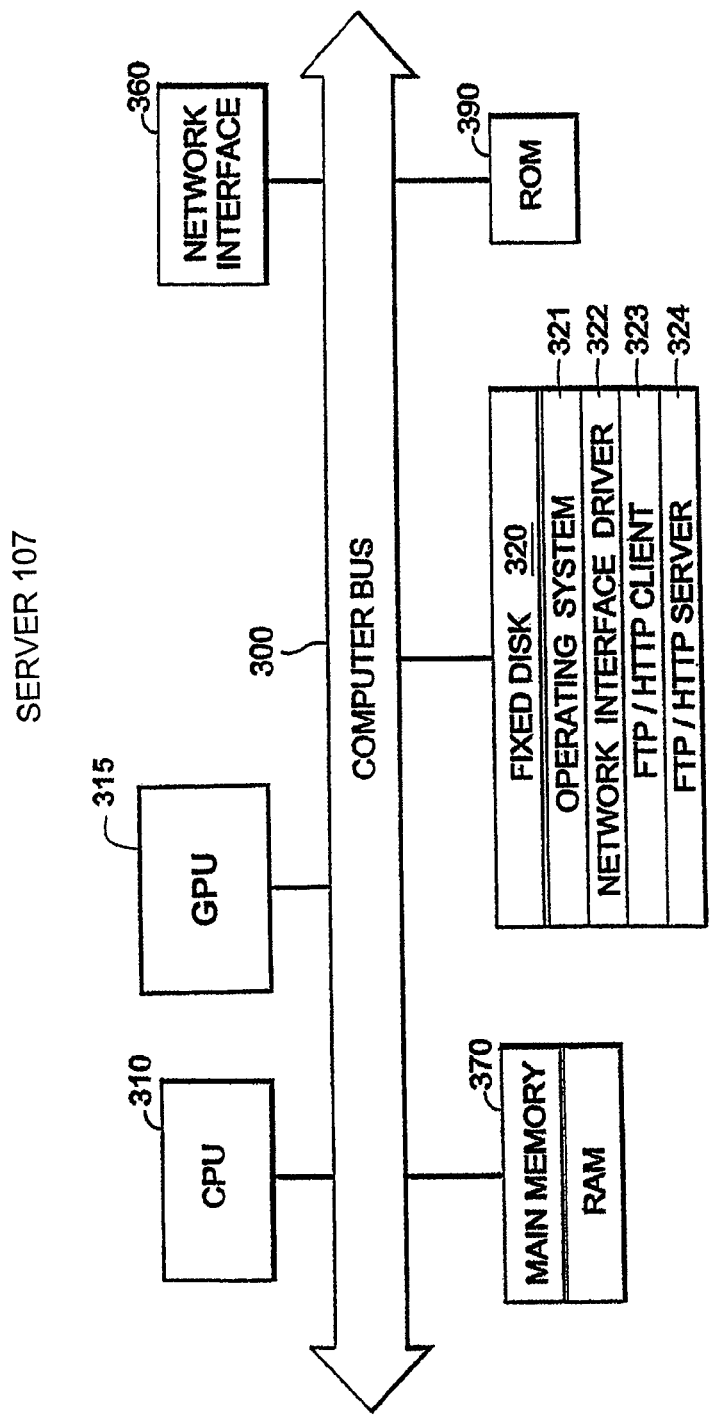
FIG. 3 depicts an internal architecture of a server.

FIG. 3 depicts a block diagram showing an overview of the internal architecture of a server, such as servers 107, 111, 121 and 131. In this regard, the internal architecture of these servers may be similar, and the description will be made merely for server 107. In FIG. 3, server 107 is seen to include a central processing unit (CPU) 310 such as a programmable microprocessor which is interfaced to computer bus 300. A graphics processing unit (GPU) 315 is also coupled to computer bus 300, where the GPU controls a graphical display program for displaying graphics on a display device. In particular, GPU 315 may implement the interactive drug advertisement/partial prescription printing processing of the invention so as to control display of the program on a display device such as display 102. Also coupled to computer bus 300 is a network interface 360 for interfacing to a network, such as WAN/Internet 140. In addition, random access memory (RAM) 370, fixed disk 320, and read-only memory (ROM) 390 are also coupled to computer bus 300. RAM 370 interfaces to computer bus 300 to provide CPU 310 with access to memory storage, thereby acting as the main run-time memory for CPU 310. In particular, when executing stored program instruction sequences, CPU 310 loads those instruction sequences from fixed disk 320 (or other memory media) into RAM 370 and executes those stored program instruction sequences out of RAM 370. It should also be recognized that standard disk-swapping techniques allow segments of memory to be swapped to and from RAM 370 and fixed disk 320. ROM 390 stores invariant instruction sequences, such as start-up instruction sequences for CPU 310 or basic input/output operating system (BIOS) sequences for the operation of peripheral devices which may be attached to server 30 (not shown).

Fixed disk 320 is one example of a computer-readable storage medium that stores program instruction sequences executable by CPU 310. The program instruction sequences may include operating system 321 and network interface driver 322. Operating system 321 can be an operating system such as Windows XP (or later versions thereof), UNIX, or other such server operating systems. Network interface driver 322 is utilized to drive network interface 360 for interfacing server 107 to network (Internet) 140.

Server 107 also preferably includes FTP/HTTP client 323 to provide server 107 with the ability to retrieve and transmit data files via FTP and HTTP protocols over the network through network interface 360. In addition, FTP/HTTP server 324 can be accessed by an FTP/HTTP client in a workstation such as workstations 106 and 112. In this regard, FTP/HTTP server 324 is preferably a web server that can be accessed by web browser application 283 to retrieve and download web pages, which are preferably comprised of an HTML document. A user wanting to access a web site to have a web page downloaded enters a URL (Uniform Resource Locator), or other type of location information where a web page may be stored, in the web browser of workstation 106, whereby the web page (in the form of an HTML document) is received by workstation 106 for display in the web browser.

Server 107 may be coupled to display device 102, which preferably includes an interactive touch screen functionality or remote control selection functionality. For instance, while server 107 may execute an interactive drug advertisement program to be displayed on display 102, server 107 may receive signals from display 102 via the touch screen or a remote control. In this manner, when various function buttons that can be selected by a patient are displayed on the display 102, a signal representing the patient's selection is transmitted to server 107, whereby the interactive program of the invention executes the selected function. One such interactive function button that may be displayed on display 102 during a drug advertisement is for the patient to print out a partial prescription for the advertised drug. In this case, a command to execute printing of the partial prescription for the advertised drug is transmitted by the display 102 to server 107, whereby the interactive program being executed by server 107 obtains a document file representing the partial prescription, activates a printer driver and converts the partial prescription document file into a printer definition language to be transmitted to printer 103. Printer 103, upon receiving the print data for the partial prescription, processed the print data and prints out the partial prescription onto a recording medium, such as paper. Here, it should be noted that the partial prescription may have data printed thereon that identifies the printer and/or interactive system manufacturer, the name of the drug, the name of the doctor's office and/or the location of the doctor's office, etc. This information may be printed on the partial prescription in a computer readable form, such as a barcode. Information that is preferably left blank on the partial prescription may be the quantity of the drug to be prescribed, the patient's name, and a signature line for the doctor to sign (i.e., confirm issuance of) the prescription to the patient.

Figure 4:
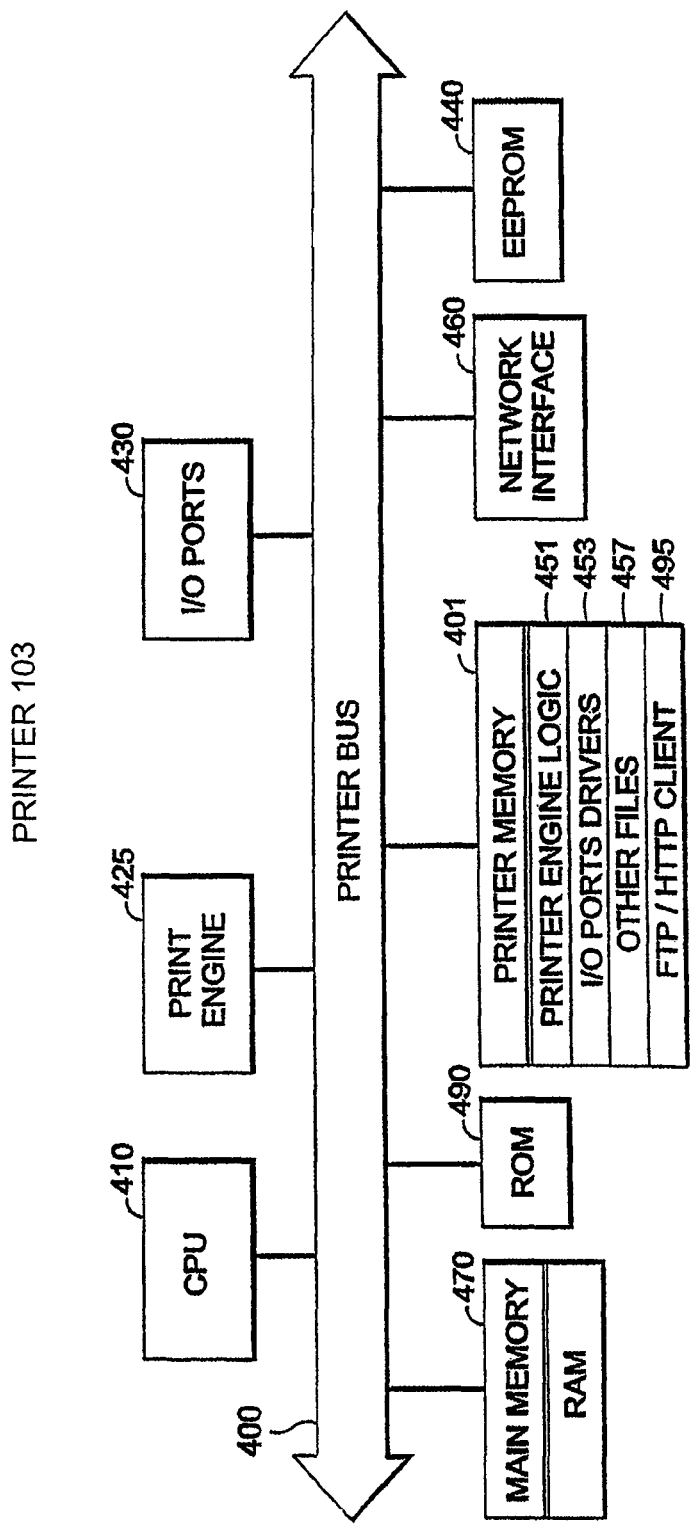
FIG. 4 depicts an internal architecture of a printer.

FIG. 4 depicts a block diagram showing an example of the internal architecture of a printer, such as printers 103 and 108. Printer 103 may receive print data from workstation 106 or server 107 to be output by the printer. For example, as discussed above, a partial prescription may be generated by computer 106 or server 107 utilizing a printer driver for printer 103 to print out the partial prescription. In FIG. 4, printer 103 is seen to contain a central processing unit (CPU) 410 such as a programmable microprocessor which is interfaced to printer bus 400. Also coupled to printer bus 400 are I/O ports 430 which is used to communicate with various input/output devices of printer 103 (not shown), and network interface 460 which is utilized to interface printer 103 to network 140.

Also coupled to printer bus 400 are EEPROM 440, for containing non-volatile program instructions, random access memory (RAM) 470, printer memory 401 and read-only memory (ROM) 490. RAM 470 interfaces to printer bus 400 to provide CPU 410 with access to memory storage, thereby acting as the main run-time memory for CPU 410. In particular, when executing stored program instruction sequences, CPU 410 loads those instruction sequences from printer memory 401 (or other memory media) into RAM 470 and executes those stored program instruction sequences out of RAM 470. ROM 490 stores invariant instruction sequences, such as start-up instruction sequences for CPU 410 or BIOS sequences for the operation of various peripheral devices of printer 30 (not shown).

Printer memory 401 is one example of a computer-readable storage medium that stores program instruction sequences executable by CPU 410 so as to constitute printer engine logic 451, I/O port drivers 453, other files 457, and e-mail program 459. Printer engine logic 451 is utilized to drive the printer engine 425 of printer 103 so as to print an image according to image data received by printer 103. I/O port drivers 453 are utilized to drive the input and output devices (not shown) connected through I/O ports 430. Other files 457 contain other files and/or programs for the operation of printer 103. Printer memory 401 also includes FTP/HTTP client 495 which provides the ability to retrieve files over the network through network interface 460.

A process for sharing revenue for the sales of prescription drugs by a drug manufacturer with a printer manufacturer according to the invention will now be described. Briefly, a patient waiting in a waiting room of a doctor's office watches drug advertisements being displayed by an interactive advertisement/printing system. If the patient sees an advertisement for a drug or medication that interests them, they utilize the interactive system to print out a partial prescription for the drug or medication. The printed-out partial prescription for the prescription drug is provided to the doctor or another individual in the doctor's office that may be authorized to issue prescriptions for medical drugs. The doctor or other authorized individual completes the partial prescription to authorize the patient to obtain the prescription drug. The completed prescription is then provided to a pharmacy for fulfillment of the completed prescription. When the pharmacy fulfills the prescription, the pharmacy transmits prescription information of the fulfilled prescription, such as the type of drug, quantity, and sales price, etc. to the prescription drug manufacturer. The prescription drug manufacturer then determines an amount of the sales revenue from the fulfillment of the prescription to provide to the printer manufacturer, and provides the determined amount to the printer manufacturer.

Figure 5:
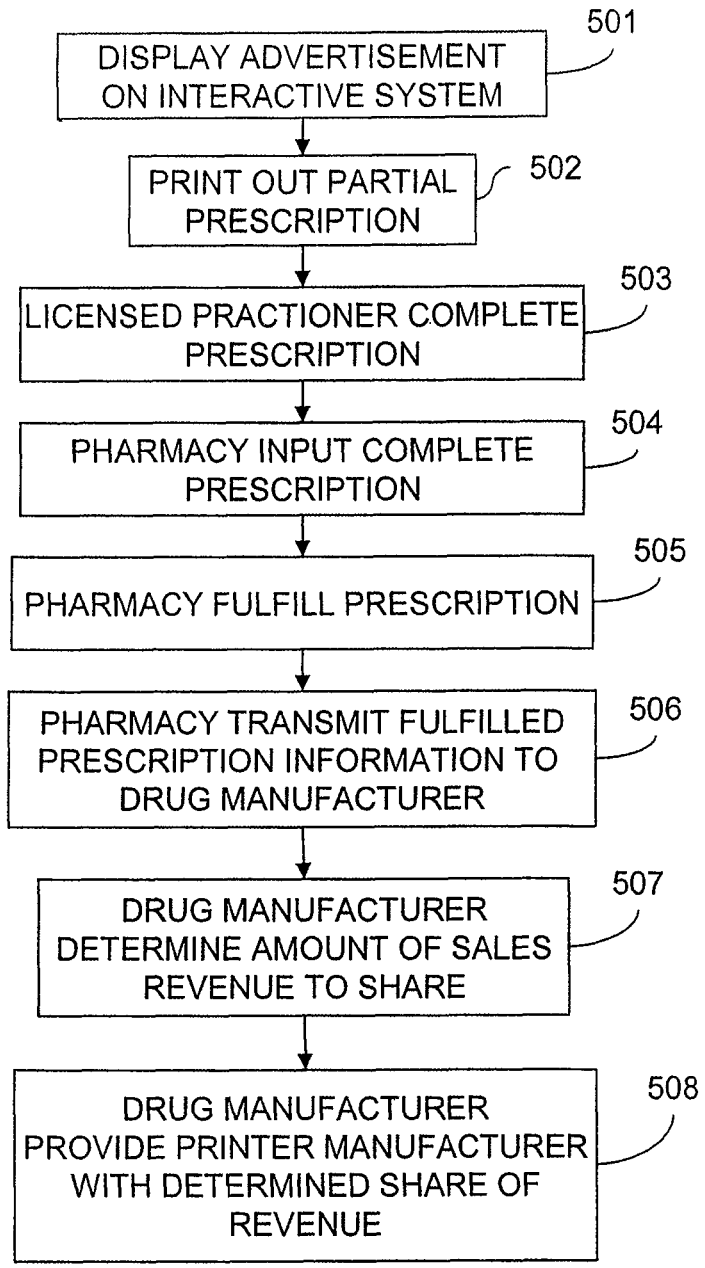
FIG. 5 is a flowchart depicting process steps for implementing the invention.

Referring to FIG. 5, depicted therein is a flowchart of process steps for the revenue sharing process of the invention. As a first step in the process of the invention, a drug or medication advertisement is displayed on an interactive display system. (step 501). As discussed above, the interactive display system is preferably installed in a waiting room of a doctor's office and may be comprised of display 102, printer 103, computer workstation 106 and/or server 107 shown in FIG. 1. A patient 105 waiting in the waiting room to visit a doctor views the drug advertisement being displayed on the interactive display/printing system. If the patient sees a drug or medication being advertised that they are interested in, and they believe they may want to obtain a prescription for the drug from the doctor, the patient utilizes the interactive system to print out a partial prescription for the drug or medication. (Step 502). Here, the patient can interact with the system by utilizing a touch screen panel on the display 102. Displayed on the display 102 may be an interactive selection button that may display, for example, "Print Partial Prescription". Alternatively, the user may utilize a pointing device, remote control, or other device that interacts with the interactive system to select the printing button, or a menu item for printing, or any other technique for printing out a partial prescription. Upon selecting the option to print out the partial prescription via the interactive system, a hard copy of a partial prescription may be printed out on, for example, printer 103.

Alternatively, or in addition to a hard copy printout of the partial prescription, an electronic version of the partial prescription may be printed to a file and sent to, for example, computer workstation 106, a doctor's wireless handheld device (not shown), server 107, etc. In this regard, upon selecting the option to print the partial prescription, the interactive system may generate an electronic document for the partial prescription, print the document to a file, and forward the print file to an office administrator, nurse, or the doctor via the computer network. By way of example, the server 107 of the interactive system may store in a database electronic templates of partial prescriptions, and when the patient selects the option to print the partial prescription, the server generates a partial prescription document by, if necessary, filling in information such as the name of the drug, and then printing the document to a file. The printed document file containing the printed partial prescription may then be forwarded to the administrator or doctor. The printed document file may be forwarded to the administrator or doctor as an attachment to an e-mail, for instance. Thus, the doctor can be provided with the partial prescription electronically. If the system also prints out a hard copy of the partial prescription, the patient 105 can simply hand the hard copy to the doctor during their examination.

The partial prescription to be printed preferably includes various information that can be read electronically. For example, the partial prescription may include a barcode that represents information of the name of the doctor, the location of the doctor's office, the name of the interactive system/printer manufacturer, and the name of the drug or medication to be prescribed. Of course, this information could also be printed in human readable form, whereby a user could read the information and input the printed information into a computer system. Alternatively, where the partial prescription is printed to a file and the file is forwarded to the doctor, an electronic header may be included with the file that includes the foregoing information such that the information can be obtained from the electronic header.

Once the doctor is provided with the partial prescription, and agrees that the drug is appropriate for the patient, the doctor completes the prescription for the patient. (Step 503). Thus, the doctor may fill-in information such as the patient's name, dosage, doctor's name and signature. In a case where the patient provides a hard copy of the partial prescription to the doctor, the doctor may manually enter the foregoing information to complete the prescription and may provide the completed hard copy of the prescription to the patient. In the case where the doctor is provided with an electronic version of the partial prescription, the doctor may enter the necessary information electronically into the electronic partial prescription file. Here, entering the information electronically may comprise the doctor utilizing a word processing program in workstation 106, for example, to enter the dosage of the drug and other information into the electronic prescription. The doctor may also utilize an electronic signature (if permitted by law) to sign the prescription. This information may also be added to the header of the electronic document, or may be provided on a hard copy of the prescription by means of a printed barcode. Once the prescription has been completed, the doctor may print out a hard copy of the completed electronic prescription on, for example, printer 108, and provide the printed hard copy of the prescription to the patient. The doctor may also, or in the alternative to providing the patient with a hard copy, forward the completed prescription electronically to a pharmacy. For example, the patient may inform the doctor of a pharmacy that they wish to have the prescription filled, whereby the doctor may send the completed prescription to a pharmacist at the designated pharmacy via e-mail or other electronic transmission. Of course, some type of security in transmitting the completed prescription could also be implemented, such as a public/private key encryption system to prevent inadvertent disclosure of the completed prescription. A system could also be implemented for the pharmacy to verify the authenticity of the electronic prescription.

Once the pharmacist receives the prescription, either by being provided with a hard copy by the patient or receiving it electronically from the doctor, the pharmacist or another authorized person of the pharmacy 110 inputs the completed prescription information into a database. (Step 504). For example, the pharmacist may enter the patient's name and contact information, the doctor's name and contact information, the name of the drug being prescribed, and the dosage being prescribed, into a database in workstation 112 or server 111 of pharmacy 110. In a case where the patient provides a hard copy of the completed prescription to the pharmacist, the pharmacist may enter the information manually into data fields displayed on a display for workstation 112. Alternatively, the pharmacist may scan a barcode on the prescription, whereby the information may be obtained therefrom and automatically input into the data fields displayed on the display for the pharmacist to review and approve. In a case where the prescription is electronically provided by the doctor's office to the pharmacy 110, the foregoing information may be automatically obtained from the electronic completed prescription file, from the header of the document, or by any other electronic means in which information may be obtained from an electronic file. Again, the automatically obtained information may be automatically input into the data fields displayed on the display for the pharmacist to approve.

With the appropriate prescription information being entered into the database at pharmacy 110, the pharmacist then fulfills the prescription. (Step 505). That is, the pharmacist obtains the prescribed dosage of the drug for the patient and provides the fulfilled prescription to the patient. As part of fulfilling the prescription, the pharmacist enters the brand of the drug issued with the prescription, along with the confirmed dosage. In addition, the patient provides pharmacy 110 with payment for the prescription. In completing the sales transaction for the prescription, the pharmacist may scan a barcode on the prescription container and may enter the sales price. This sales information may then be stored in the database in correlation with the information input in step 504.

Once the prescription has been fulfilled, pharmacy 110 transmits the sales information to the drug manufacturer (Step 506). In this regard, the sales information may be transmitted coincident with completion of the sales transaction, or the pharmacy may transmit sales information to the drug manufacturer periodically (e.g., once a day, once per week, once per month, etc.). The information may be transmitted by, for example, server 111 to server 121 of drug manufacturer 120 via network 140. The sales information preferably includes at least the name of the drug, the price of the sale, the name of the doctor, and the location of the doctor's office. The information may also include the name of the interactive advertising/printer system which was printed on the partial prescription. With this information having been provided to the drug manufacturer 120, the drug manufacturer can then determine what portion of the sales revenue is to be shared with the interactive advertising/printing system manufacturer 130. (Step 507). The portion to be allotted to the printer manufacturer may be determined based on a revenue sharing agreement between the printer manufacturer and the drug manufacturer. The determination may be conducted automatically by a revenue sharing program in server 121. Once the amount of sales revenue to be shared with the printer manufacturer has been determined, the determined amount can then be provided to printer manufacturer 130. (Step 508). In this regard, server 121 can credit an account of printer manufacturer, may transmit an amount of electronic money to server 131 or to a bank account of printer manufacturer 130. Alternatively, an administrator of drug manufacturer 120 may generate a check and send it to printer manufacturer 130.

Thus, as can be seen from the foregoing, printer manufacturers can share in the revenue for the sales of prescription drugs. Additionally, by being provided with the sales information, including the name of the drug, the location of the doctor's office, etc., the drug manufacturer can track which drugs are prescribed more often in various geographic regions, thereby allowing the drug manufacturer to adjust their marketing and advertising plans for each geographic region. The drug manufacturers can also track the effectiveness of the interactive advertising systems based on the volume of prescriptions fulfilled at any given doctor's office.

The invention has been described with particular illustrative embodiments. It is to be understood that the invention is not limited to the above-described embodiments and that various changes and modifications may be made by those of ordinary skill in the art without departing from the spirit and scope of the invention.

What is claimed is:

1. A non-transitory computer-readable storage medium on which is stored a computer program to be executed by a computer system for sharing in a revenue for a sale of prescription drugs through a partial prescription handout based on an advertisement of the prescription drugs, the computer program comprising instructions of:
    specifying a prescription drug requiring a prescription to purchase being displayed and advertised on a display unit;
    providing a conversion rule for converting, into a predetermined form, information regarding the specified prescription drug and information regarding a provider of a printer for printing out a partial prescription corresponding to the specified prescription drug;
    providing the converted information which have been converted by the conversion rule for being attached to a partial prescription handout;
    providing a reconversion rule for reconverting the information converted and attached to the handout;
    reading out, from a memory, sales information regarding a portion of the revenue to be shared for the prescription drug set based on an agreement between a seller of the specified prescription drug and the provider of the printer; and
    notifying the provider of the printer, in response to detection of fulfillment for a complete prescription based on the partial prescription handout, of the portion of the revenue to be shared to the provider of the printer based on the reconverted information of the provider,
    wherein the complete prescription is completed by an individual authorized to issue prescriptions based on the partial prescription.

2. The non-transitory computer-readable storage medium according to claim 1, wherein the predetermined form is a bar code.

3. The non-transitory computer-readable storage medium according to claim 1, wherein the printer is located in a medical office associated with the individual authorized to issue the prescriptions.

4. The non-transitory computer-readable storage medium according claim 1, wherein the printer is connected to an interactive touch-screen television and wherein the partial prescription is printed out by an operation of a patient utilizing the touch-screen television.

5. The non-transitory computer-readable storage medium according to claim 4, wherein a hard copy of the partial prescription is printed-out by the printer and the patient provides the hard copy printout to the individual authorized to issue prescriptions.

6. The non-transitory computer-readable storage medium according to claim 4, wherein the partial prescription is printed to an electronic file, and the electronic file is electronically transmitted to the individual authorized to issue prescriptions.

7. The non-transitory computer-readable storage medium according to claim 6, wherein the partial prescription is electronically completed, and the complete prescription is provided to a pharmacy via an electronic transmission.

8. The non-transitory computer-readable storage medium according to claim 7, wherein the information of the completed prescription from the electronically transmitted prescription is obtained automatically and the obtained information is input into a database.

9. The non-transitory computer-readable storage medium according to claim 1, wherein the partial prescription includes a name of the prescription drug and includes blank spaces for a patient's name, dosage and a signature of the individual authorized to issue prescriptions.

10. The non-transitory computer-readable storage medium according to claim 1, wherein the partial prescription is printed with a bar code associated with the provider of the printer.

11. The non-transitory computer-readable storage medium according to claim 10, wherein the bar code is scanned-in and information corresponding to the bar code is transmitted to the printer provider associated therewith, along with a sales amount for the prescription to the prescription drug seller.

12. The non-transitory computer-readable storage medium according to claim 1, wherein a record of the number and type of prescriptions fulfilled by a pharmacy is maintained in correspondence with identification information of the printer.

13. A method executed by a computer system for sharing in a revenue for a sale of prescription drugs through a partial prescription printed out based on an advertisement of the prescription drugs, the method comprising:
    specifying a prescription drug requiring a prescription to purchase being displayed and advertised on a display unit;
    providing a conversion rule for converting, into a predetermined form, information regarding the specified prescription drug and information regarding a provider of a printer for printing out a partial prescription corresponding to the specified prescription drug;
    providing the converted information which have been converted by the conversion rule for being attached to a partial prescription handout;
    providing a reconversion rule for reconverting the information converted and attached to the handout;

reading out, from a memory, sales information regarding a portion of the revenue to be shared for the prescription drug set based on an agreement between a seller of the specified prescription drug and the provider of the printer; and notifying the provider of the printer, in response to detection of fulfillment for a complete prescription based on the partial prescription handout, of the portion of the revenue to be shared to the provider of the printer based on the sales information for the prescription drug corresponding to the fulfilled prescription, wherein the complete prescription is completed by an individual authorized to issue prescriptions based on the partial prescription.

* * * * *